United States Patent [19]

Hughes et al.

[11] 4,433,053

[45] Feb. 21, 1984

[54] FERMENTATION PROCESS FOR THE PRODUCTION OF POLY(β-HYDROXY BUTYRIC ACID)

[75] Inventors: Lorenzo Hughes, Yarm; Kenneth R. Richardson, Middlesbrough, both of England

[73] Assignee: Imperial Chemical Industries PLC, London, England

[21] Appl. No.: 291,762

[22] Filed: Aug. 10, 1981

[30] Foreign Application Priority Data

Aug. 19, 1980 [GB] United Kingdom ............... 8027004

[51] Int. Cl.$^3$ .................. C12P 7/52; C12P 7/44; C12P 7/42; C12N 1/38
[52] U.S. Cl. ................... 435/141; 435/142; 435/146; 435/244; 435/829
[58] Field of Search ............ 435/141, 142, 146, 136, 435/132, 244, 247, 135, 829

[56] References Cited

U.S. PATENT DOCUMENTS

| | | | |
|---|---|---|---|
| 3,044,942 | 7/1962 | Baptist | 435/146 |
| 4,140,741 | 2/1979 | Lafferty et al. | 435/146 |
| 4,211,846 | 7/1980 | Lafferty | 435/146 |
| 4,336,334 | 6/1982 | Powell et al. | 435/146 |

OTHER PUBLICATIONS

Sonnleitner et al., "Formal Kinetics of PHB Production in *A.eutrophus* H16 and *M.rubra* R14", *Euro. J. Appl. Microbiol. Biotechnol.*, 7; 1979; pp. 1-10.
Schlegel et al., "Formation and Utilization of PHB by Knallgas Bacteria", *Nature*, vol. 191, Jul. 29, 1961; pp. 463-465.
Hepfinstall et al., "Effect of Growth Conditions on Morphology of *Hydrogenomonas facilis* and on Yield of a Phospholipoprotein; *J. Bacteriology*, vol. 110; 1972; pp. 363-367.
Voytovich et al.; "Autotrophic Growth of Hydrogen Bacteria in Continuous Culture", *Z.f. Allg. Mikrobiologie;* vol. 12, No. 1, 1972; pp. 69-73.
Bongers, Leonard; "Yields of *Hydrogenomonos eutropha* from Growth on Succinate and Fumarate", *J. Bacteriology*, May 1970; pp. 598-599.
Gottschalk, G.; *Bacterial Metabolism*, Springer-Verlag, ©1979, pp. 107, 108.

*Primary Examiner*—Raymond N. Jones
*Assistant Examiner*—Elizabeth J. Curtin
*Attorney, Agent, or Firm*—Cushman, Darby & Cushman

[57] ABSTRACT

Continuous fermentation of *Alcaligenes* micro-organisms capable of accumulating PHB under limitation of a nutrient required for growth, but not PHB accumulation, so that the PHB content is above 25% by weight. By means of this the carbon in the carbon and energy source, i.e. the substrate, is utilized more efficiently.

10 Claims, No Drawings

FERMENTATION PROCESS FOR THE PRODUCTION OF POLY(β-HYDROXY BUTYRIC ACID)

This invention relates to a fermentation process and in particular to a process for the production of poly(β-hydroxy butyric acid), hereinafter referred to as PHB.

PHB is accumulated by many bacteria within their cells as an energy reserve material. PHB is a thermoplastic polyester and as such it is of use as a plastics material.

When PHB-accumulating micro-organisms are aerobically cultured on a suitable substrate, i.e. a source of energy and carbon, they reproduce until one or more of the essential requirements for reproduction is exhausted. This reproduction of the micro-organism is hereinafter referred to as growth. Upon exhaustion of an essential growth requirement, further growth occurs only to a very limited extent, if at all, but, providing the substrate is not exhausted, PHB may be accumulated by the micro-organism.

With some micro-organisms, even in the absence of a PHB-inducing constraint such as a limitation on one or more of the essential growth requirements, PHB may also be accumulated while growth of the micro-organism is taking place; however the amount of PHB so accumulated is generally small and typically is less than about 10% by weight of the cells produced. Thus, when grown in batch culture, the micro-organism will grow, with little or no PHB accumulation until one or more of the essential requirements for growth becomes limiting and then exhausted, and then the micro-organism synthesises PHB. In the growth stage the carbon conversion is generally below about 60% since some carbon in the substrate is oxidised to carbon dioxide to provide the energy required for the micro-organism to grow.

By the term carbon conversion we mean the ratio of the number of gram atoms of carbon in the product to the number of gram atoms of carbon in the substrate used to produce that product. Thus at 60% carbon conversion, 1 mole (6 gram atoms of carbon) of glucose would give 3.6 gram atoms of carbon in the product, i.e. 43.2 g of combined carbon. Depending on the PHB content of the product, the carbon content thereof will range between about 47 and 53% by weight and so the amount of product produced from 1 mole (180 g) of glucose at 60% carbon conversion will be between about 82 and 92 g.

Likewise in the PHB accumulation stage the carbon conversion (substrate carbon to PHB carbon) is also generally below about 60% when using glucose as a substrate. We have found that in the PHB accumulation stage, the carbon conversion falls as the PHB content of the cells rises above approximately 50% by weight.

Since the raw material, i.e. substrate, cost is a significant factor in the overall cost of PHB production it would clearly be desirable to achieve higher carbon conversions.

We have found that with certain micro-organisms the overall carbon conversion may be increased if the fermentation is conducted under conditions such that both growth and PHB accumulation occur at the same time.

Micro-organisms that may be used include the PHB-accumulating micro-organisms of the Alcaligenes genus, for example *A. faecalis, A. ruhlandii, A. latus, A. aquamarinus*, and *A. eutrophus*. These species have been described in the literature and various strains thereof are listed in culture collection catalogues. Exemplary strains listed in the catalogue of the American Type Culture Collection, 12301 Park Lawn Dr., Rockville, Md. 20852, U.S.A. are

| | |
|---|---|
| A. facecalis | ATCC 8750 |
| A. ruhlandii | ATCC 15749 |
| A. latus | ATCC 29712 |
| A. aquamarinus | ATCC 14400 |
| A. eutrophus | ATCC 17699 |

*A. eutrophus*, previously known as *Hydrogenomonas eutropha*, is the preferred micro-organism, e.g. strain H 16 which has been widely employed in academic studies of this species, see e.g. J General Microbiology (1979) 115 pages 185–192, and which is available as the aforesaid ATCC strain 17699, and mutants of strain H 16 such as mutants 11/7B, S301/C5, S501/C29 and S501/C41, which have been deposited with the National Collection of Industrial Bacteria, Torry Research Station, Aberdeen, Scotland, under NCIB Nos. 11600, 11599, 11597 and 11598 respectively, on Aug. 18, 1980.

The effect is not shown with other types of PHB-accumulating micro-organisms such as *Azobacter chroococcum*, e.g. strain NCIB 9125, *Methylobacterium organophilum*, e.g. strains NCIB 11482–11488 inclusive, and ATCC 27886, and Pseudomonas AM1 e.g. strain NCIB 11489.

Micro-organisms such as *Alcaligenes eutrophus* are capable of growth, and PHB accumulation, by aerobic fermentation using a mixture of hydrogen and carbon dioxide as the substrate. With such a substrate the cost of the hydrogen is a major factor whereas carbon dioxide is relatively cheap: hence increased carbon conversion using such a substrate is of little significance. However, these micro-organisms are also capable of using a variety of other substrates in which the hydrogen and carbon are combined, generally together with oxygen. Examples of such substrates include organic acids or salts thereof, e.g. formates, acetates, oxalates, pyruvates, and carbohydrates such as fructose. While *Alcaligenes eutrophus* strain H 16 (ATCC 17699) will not utilise glucose, certain mutants thereof e.g. the aforesaid mutants 11/7B, S301/C5, S501/C29 and S501/C41 can use glucose. Carbohydrates, particularly glucose, are the preferred substrates in view of the cost and the fact that the micro-organisms can grow efficiently thereon.

In order to obtain the benefit of improved carbon conversion, the fermentation is conducted under conditions such that both growth and PHB accumulation occur at the same time. This is not possible to any significant extent in a batch fermentation process, but can be achieved in a continuous fermentation process by restricting the amount supplied to the fermenter of one or more of the essential nutrients that is required for growth but not for PHB accumulation.

Accordingly we provide a fermentation process for the production of PHB-containing bacterial cells comprising aerobically culturing a PHB-accumulating micro-organism of the Alcaligenes genus continuously in a fermentation vessel to which (a) an aqueous medium containing nutrient salts and (b), as a carbon and energy source, a water soluble compound that is assimilable by the micro-organism and which contains at least carbon and hydrogen are continuously or intermittently supplied and continuously or intermittently removing aqueous medium containing the bacterial cells from the vessel so as to maintain the amount of aqueous medium in the vessel substantially constant, the amount of at least one of the essential requirements for growth of the micro-organism, but not for accumulation of PHB, supplied to the vessel being restricted such that the bacterial cells removed therefrom contain, on average, at least 25% by weight of PHB.

In addition to the substrate and oxygen (which is generally supplied by injecting air into the aqueous medium in the fermenter), various nutrient salts are required to enable the micro-organism to grow. Thus sources of the following elements in assimilable form, normally as water soluble salts, are generally required: nitrogen, phosphorus, sulphur, potassium, sodium, magnesium, calcium, and iron, together with traces of elements such as manganese, zinc and copper. While it may be possible to induce PHB accumulation by restricting the supply of oxygen to the fermenter, it is preferred to restrict the amount of one or more of the nutrient salts. The most practical elements to limit are nitrogen, phosphorus, or, less preferably, magnesium, sulphur or potassium. Of these it is most preferred to restrict the amount of nitrogen (which is conveniently supplied as an ammonium salt). The amount of assimilable nitrogen required is about 8-15% by weight of the desired weight of cells less PHB.

In order to obtain the benefits of increased carbon conversion, the cells removed from the fermenter should have a PHB content of at least 25% by weight: below this figure the improvement in carbon conversion becomes less significant.

The proportion of PHB accumulated in the cells depends, inter alia, on the average residence time of the medium containing the suspended micro-organism in the fermenter. Providing sufficient substrate is supplied, the greater the residence time the greater will be the PHB content. To obtain the optimum carbon conversion at any desired PHB content, the amount of substrate employed should be kept to the minimum that is consistent with economic operation. In general it is desirable to have a slight excess of substrate, preferably at least 1 g per liter, and in particular 2 to 5 g per liter, so that there is a small concentration of residual substrate in the aqueous medium removed from the fermenter.

While the micro-organisms are capable of accumulating relatively high proportions of PHB, e.g. up to 75-80% by weight based on the total weight of the bacterial cells, the residence time to achieve such a high PHB content will generally be uneconomically lengthy. Hence it is preferred that the residence time is such that the PHB content is less than 70%, and in particular is between 35 and 65%, by weight.

The fermenter is preferably operated so that the dry weight of the PHB-containing cells is at least 5 g per liter of aqueous medium. Hence if, for example, it is desired to produce 10 g per liter of PHB-containing cells having a PHB content of 40% by weight, the amount of the essential nutrient fed to the fermenter that is used to limit the amount of cell growth must be that required to support the growth of 6 g per liter of cells containing no PHB; thus, if nitrogen is employed as the growth limiting nutrient, since the nitrogen content of PHB free bacterial cells is about 8-15% by weight, the amount of assimilable nitrogen required would be between about 0.5 and 0.9 g per liter, e.g. about 0.6 to 1.2 g of ammonium ions per liter.

The fermentation may be conducted under the conditions e.g. pH, temperature, and degree of aeration (unless oxygen is utilised as the limiting nutrient) conventionally used for the micro-organism. Likewise the amounts of nutrient salts (other than the growth limiting nutrient whose amount may be determined following the considerations outlined hereinbefore) employed may be those normally used for growth of the micro-organism.

Aqueous medium containing the bacterial cells is continuously, or intermittently, removed from the fermenter at a rate corresponding to the rate of addition of fresh aqueous medium to the fermenter. The aqueous medium having the bacterial cells suspended therein removed from the fermenter may be subjected to suitable treatment to extract the PHB from the bacterial cells (or where the PHB-containing cells are to be used as a moulding material, the cells may simply be separated from the aqueous medium).

Alternatively, before such a PHB extraction and/or water separation step, the aqueous medium containing the bacterial cells may be fed to a further fermenter or fermenters (which may be operated in batch or continuous fashion) wherein further PHB accumulation is caused to take place. While additional quantities of substrate and nutrient salts may be added in this further fermentation step, since further growth is generally not desired, little or no further quantity of the nutrient utilised to limit growth in the first fermentation should be added. It will however be appreciated that the aqueous medium fed to the further fermenter or fermenters from the first fermenter may contain some residual quantity of the limiting nutrient and/or the addition of a further small quantity thereof may be desirable for efficient operation. In the further fermentation step, the PHB content of the bacterial cells is preferably increased to between 50 and 80% by weight.

The substrate employed in the further fermentation may be the same as, or different to, that used in the first fermentation. In some cases the overall efficiency of the process may be increased by utilising in the first fermentation a substrate, such as a carbohydrate, that is fairly efficiently converted to both cell material and PHB while in the second stage the substrate is a material, such as an organic acid or salt thereof, e.g. an acetate, which is converted efficiently to PHB but on which the micro-organism grows less efficiently.

The PHB is produced as granules inside the micro-organism cells. While the cells containing PHB may themselves be used as a moulding material, for example as described in U.S. Pat. No. 3,107,172, it is generally desirable to separate the PHB from the bacterial cells. This may be accomplished by subjecting the cells to a cell breakage step followed by extraction of the PHB with a suitable solvent. Examples of suitable extraction processes are described in our European Patent Application No. 15123.

The invention is illustrated by the following examples in which all percentages are expressed by weight.

EXAMPLE 1 (Comparative)

3.5 liters of an aqueous medium A and 35 g of fructose were charged to a stirred fermenter of 5 liters nominal capacity and maintained at 30° C.

Medium A had the following composition, per liter of deionised water:

| | |
|---|---|
| (NH$_4$)$_2$SO$_4$ | 8.65 g |
| H$_3$PO$_4$ (1.1 M) | 18 ml |
| MgSO$_4$.7H$_2$O | 0.6 g |
| K$_2$SO$_4$ | 1.5 g |
| FeSO$_4$.7H$_2$O | 1 g |
| Trace element solution | 48 ml |

The trace element solution had the composition:

| | | |
|---|---|---|
| Calcium | 720 mg l$^{-1}$ | |
| Copper | 5 mg l$^{-1}$ | as soluble |
| Manganese | 24 mg l$^{-1}$ | salts |
| Zinc | 22 mg l$^{-1}$ | |

The medium was innoculated with a starter culture of *Alcaligenes eutrophus* H 16 (ATCC 17699) and fermentation conducted aerobically at a dissolved oxygen tension of about 60% air saturation. During fermentation the pH was maintained automatically at 6.8 by addition of 4 M NaOH. Periodically further quantities of fructose were added to maintain an excess of substrate. After a total of 70 hours fermentation the concentration of cells, which contained about 70% PHB, was about 45 g l$^{-1}$. The yield of cells was about 0.45 g per g of fructose which corresponds to a carbon conversion of about 57%.

EXAMPLE 2 (comparative)

The procedure of Example 1 was repeated using a glucose utilising mutant (mutant S301/C5) of *Alcaligenes eutrophus* with glucose being used in place of fructose. In this fermentation the temperature was maintained at 34° C. After 70 hours fermentation the cell concentration was again about 45 g l$^{-1}$ and the PHB content of the cells about 70%. The yield of cells was 0.42 g per g of glucose which corresponds to a carbon conversion of about 54%.

EXAMPLE 3

Example 1 was repeated but using in place of medium A, a medium B having the following composition, per liter of deionised water:

| | |
|---|---|
| (NH$_4$)$_2$SO$_4$ | 2 g |
| H$_3$PO$_4$ (1.1 M) | 12 ml |
| MgSO$_4$.7H$_2$O | 0.8 g |
| K$_2$SO$_4$ | 0.45 g |
| FeSO$_4$.7H$_2$O | 7.5 mg |
| Trace element solution (as in Example 1) | 24 ml |

After a period of batch fermentation, continuous fermentation was established by continuously removing medium containing cells from the fermenter and continuously replacing it with an equivalent amount of fresh medium B to which about 16 g l$^{-1}$ of fructose had been added. After a period of time steady state conditions were reached and maintained for two weeks. At the steady state, the amount of medium removed was 350 ml hr$^{-1}$ giving a dilution rate, i.e. reciprocal of residence time, of 0.1 hr$^{-1}$.

EXAMPLE 4

The procedure of Example 3 was repeated using the glucose mutant (mutant S301/C5) of *Alcaligenes eutrophus* and using glucose in place of fructose. In this fermentation the temperature was maintained at 34° C. The amount of glucose added to the medium B continuously fed to the fermenter was about 15 g l$^{-1}$.

The results are shown in the following table.

| | | Ex 3 | Ex 4 |
|---|---|---|---|
| Micro-organism | | H 16 | mutant S301/C5 |
| Substrate | | fructose | glucose |
| Temperature | °C. | 30 | 34 |
| Dilution rate | hr$^{-1}$ | 0.1 | 0.1 |
| Substrate feed concentration | g l$^{-1}$ | 15.88 | 14.89 |
| Residual* substrate concentration | g l$^{-1}$ | 6.85 | 3.44 |
| Amount of substrate utilised | g l$^{-1}$ | 9.03 | 11.45 |
| Residual* nitrogen concentration | ppm N | <1 | <1 |
| Cell dry weight | g l$^{-1}$ | 5.19 | 6.21 |
| PHB content | % | 30 | 47 |
| Cell yield | g per g substrate | 0.575 | 0.542 |
| Carbon conversion to cells | % | 71 | 69 |

*residual concentration is the concentration in the medium that is continuously removed from the fermenter.

It is seen that the carbon conversions are significantly greater than those achieved in batch fermentation (cf Examples 1 and 2). By way of comparison studies of single stage continuous culture of a *Methylobacterium organophilum* strain (NCIB 11483) on methanol under nitrogen limitation gave a maximum carbon conversion to cells of 53% at a dilution rate of 0.08 hr$^{-1}$. Under these conditions the maximum PHB content achieved was about 11%.

Likewise batch culture studies of this micro-organism on methanol gave a maximum PHB content of 45% after 60 hours fermentation with a cell yield of 0.16 g per g methanol representing a carbon conversion to cells of 21%.

Single stage continuous culture studies using *Azotobacter chroococcum* (NCIB 9125) on glucose under nitrogen limitation gave a maximum carbon conversion to cells of the order of 22–25% at a dilution rate of 0.09 hr$^{-1}$. Under these conditions the PHB content varied between only 1 and 6%. When working under oxygen limitation, i.e. by having ample nitrogen (as ammonium ions) in the medium but using an aeration flow rate of 0.1 volumes of air per volume of medium in the fermenter per minute, so giving a dissolved oxygen tension of zero, at a dilution rate of 0.1 hr$^{-1}$, an initial carbon conversion to cells of 60% was achieved, but after 8 days operation the carbon conversion dropped to 50%. During the same period the PHB content of the cells dropped from 51% to 30%.

Likewise batch cultures of *Azotobacter chroococcum* (NCIB 9125) under oxygen limitation after 60–65 hours fermentation gave cells having a maximum PHB content of about 65% at a maximum carbon conversion of about 35%.

EXAMPLE 5

The medium continuously removed from the fermenter in Example 4 was continuously fed, together with a further 15 g l$^{-1}$ of glucose, to a second fermenter of nominal capacity 10 liters and a second fermentation performed, again at 34° C., pH 6.8, dissolved oxygen tension about 60% air saturation.

When the total amount of medium fed to the second fermenter reached 7 liters, medium was removed from the second fermenter at a rate corresponding to the rate of addition from the first fermenter so as to give a second stage dilution rate of 0.05 hr$^{-1}$.

After a period of time steady state conditions were achieved and maintained for 2 weeks. The average cell content of the medium removed from the second fermenter (when in steady state operation) was 10.91 g l$^{-1}$ with a PHB content of about 70–75%. The carbon conversion in the second stage was about 45%.

The overall carbon conversion of both stages was 57.9% to cells (i.e. total glucose carbon to total cell carbon) and 43.8% to PHB (i.e. total glucose carbon to PHB carbon).

EXAMPLE 6

To provide a comparison between a fermentation operated under nitrogen limitation, i.e. in accordance with the present invention, and with a fermentation operated under carbon limitation (not in accordance with the present invention since carbon is an essential requirement for both growth and PHB accumulation), two identical laboratory fermenters, of working volume 2 liters maintained at 34° C. were set up.

The aqueous medium employed had the following composition, per liter of de-ionised water,

| | |
|---|---|
| 5% NH$_4$OH solution | 6.4 ml (= 750 mg N) |
| H$_3$PO$_4$ (1.1 M) | 12 ml |
| MgSO$_4$.7H$_2$O | 0.8 g |
| FeSO$_4$.7H$_2$O | 4.17 mg |
| Trace element solution (as in Example 1) | 36 ml |

Potassium and sodium were supplied via the pH control using a mixture of 9 volumes of 4 M KOH to 1 volume of 4 M NaOH.

The media were inoculated with a starter culture of the glucose utilising mutant S301/C5 of *Alcaligenes eutrophus* and the fermentation conducted aerobically using glucose as the substrate at a dissolved oxygen tension of between 50 and 80% of air saturation. The pH was maintained automatically at 6.8 by addition of the KOH/NaOH solution.

After a period of batch fermentation, continuous fermentation was established by continuously removing aqueous medium containing cells from the fermenter and continuously replacing it with an equivalent amount of fresh medium and glucose. In the steady state conditions which were maintained for several weeks, the dilution rate of both fermentations was 0.085±0.005 hr$^{-1}$.

One fermenter was maintained under nitrogen limitation by feeding glucose at such a rate that the residual nitrogen level was less than 1 mg l$^{-1}$ and the residual glucose level was between 2 and 3 g l$^{-1}$. The other fermenter was maintained under carbon limitation by feeding glucose at such a rate that the residual glucose level was less than 0.5 g l$^{-1}$ and the residual nitrogen level was above 100 mg l$^{-1}$.

At the steady state conditions, the results were as shown in the following table (these results are an average of several weeks data):

| | | Fermentation A | Fermentation B |
|---|---|---|---|
| limitation | | nitrogen | carbon |
| dilution rate | h$^{-1}$ | 0.084 | 0.083 |
| glucose feed concentration | g l$^{-1}$ | 26.3 | 10.25 |
| residual glucose concentration | g l$^{-1}$ | 2.5 | 0.15 |
| glucose utilised | g l$^{-1}$ | 23.8 | 10.1 |
| residual nitrogen concentration | mg l$^{-1}$ | 0.5 | 165 |
| cell dry weight | g l$^{-1}$ | 11.92 | 5.05 |
| PHB content | % | 55 | 5 |
| cell carbon content | % | 52 | 47 |
| carbon conversion to cell carbon | % | 65 | 59 |

We claim:

1. A continuous fermentation process for the production of bacterial cells containing poly (β-hydroxy butyric acid), comprising (i) continuously or intermittently supplying to a fermentation vessel containing a poly (β-hydroxy butyric acid)-accumulating micro-organism of the Alcaligenes genus, a micro-organism-free feed containing (a) an aqueous medium containing nutrient salts and (b), as a carbon and energy source, a water soluble compound that is assimilable by the micro-organism and which contains at least carbon and hydrogen, wherein said micro-organism-free feed includes a restricted amount of at least one of the elements selected from the group consisting of assimilable nitrogen, phosphorus, magnesium, sulphur and potassium, which elements are essential to growth of the micro-organism but not to accumulation of poly (β-hydroxy butyric acid), (ii) aerobically cultivating said micro-organism in said vessel so that it grows and accumulates poly (β-hydroxy butyric acid), and (iii) continuously or intermittently removing an equivalent amount of aqueous medium containing bacterial cells from the vessel so as to maintain the amount of aqueous medium in the vessel substantially constant, said restricted amount of elements being such that the bacterial cells removed from said vessel contain at least 25% by weight of poly (β-hydroxy butyric acid).

2. A process according to claim 1 wherein the essential requirement for growth is selected from assimilable nitrogen and phosphorus.

3. A process according to claim 2 wherein the essential requirement for growth that is restricted is nitrogen and the amount of assimilable nitrogen that is supplied to the fermentation vessel is from 8 to 15% by weight of the difference between the amount of bacterial cells removed from the fermentation vessel and the amount of PHB accumulated in said removed bacterial cells.

4. A process according to claim 1 wherein the bacterial cells removed from the vessel contain from 35 to 65% by weight of PHB.

5. A process according to claim 1 wherein the aqueous medium removed from the vessel contains at least 5 g per liter of bacterial cells.

6. A process according to claim 1 wherein the aqueous medium removed from the vessel contains a residual amount of at least 1 g per liter of said water soluble compound forming the carbon and energy source.

7. A process according to claim 11 wherein the aqueous medium containing the bacterial cells removed from the vessel is fed to a further fermentation vessel together with, as a carbon and energy source, a water soluble compound that is assimilable by the micro-organism and which contains at least carbon and hydrogen, and the micro-organism is aerobically cultured in said further fermentation vessel so as to increase the PHB content of the bacterial cells.

8. A process according to claim 7 wherein no additional quantity of said essential requirement for growth whose supply to the first fermentation vessel is restricted, over any residual quantity remaining in the aqueous medium removed from the first fermentation vessel, is supplied to said further fermentation vessel.

9. A process according to claim 7 wherein the culturing of the micro-organism in said further fermentation vessel is continuous.

10. A process according to claim 7 wherein the culturing of the micro-organism in said further fermentation vessel is continued until the bacterial cells have a PHB content within the range 50 to 80% by weight.

* * * * *